United States Patent [19]

Shah et al.

[11] 4,307,242

[45] Dec. 22, 1981

[54] PROCESS FOR REMOVING IMPURITIES FROM RESIDUAL SILICON POWDER

[75] Inventors: Bakulesh N. Shah, Clifton Park; Alan Ritzer, Sand Lake, both of N.Y.

[73] Assignee: General Electric Company, Waterford, N.Y.

[21] Appl. No.: 209,635

[22] Filed: Nov. 24, 1980

Related U.S. Application Data

[63] Continuation-in-part of Ser. No. 193,761, Oct. 3, 1980, abandoned.

[51] Int. Cl.³ .............................. C07F 7/16; C07F 7/08
[52] U.S. Cl. .................................. 556/472; 556/473; 422/198; 422/199
[58] Field of Search ........................ 556/472; 556/473

[56] References Cited

U.S. PATENT DOCUMENTS

| | | | |
|---|---|---|---|
| 2,389,931 | 11/1945 | Reed et al. | 556/473 X |
| 2,803,521 | 8/1957 | Nitzsche et al. | 556/472 X |
| 3,133,109 | 5/1964 | Dotson | 556/472 |
| 3,536,743 | 10/1970 | Schrader et al. | 556/472 |
| 3,560,545 | 2/1971 | Schrader et al. | 556/472 |
| 3,655,709 | 4/1972 | Fries et al. | 556/472 |
| 4,218,387 | 8/1980 | Maas et al. | 556/472 |

*Primary Examiner*—Paul F. Shaver
*Attorney, Agent, or Firm*—M. J. Doyle; Philip L. Schlamp

[57] ABSTRACT

A process for recovering and recycling elementary silicon from a direct process organohalosilane reactor system is provided, comprising the steps of analyzing a portion of effluent contact mass, such as the silicon fines from a secondary cyclone with a particle size distribution analyzer, determing the fines fractions containing the relatively greatest amounts of impurities and segregating a relatively impure fine fraction from a purer coarse fraction with the aid of an aerodynamic centrifugal classifier.

10 Claims, 3 Drawing Figures

PROCESS FOR REMOVING IMPURITIES FROM RESIDUAL SILICON POWDER

CROSS REFERENCE TO RELATED APPLICATION

This application is a Continuation-In-Part of U.S. application Ser. No. 193,761 of SHAH and RITZER, filed Oct. 3, 1980, and now abandoned.

BACKGROUND OF THE INVENTION

The present invention relates to the production of chlorosilanes and more particularly to a process for recovering elementary silicon from residual silicon powder and recycling pure silicon.

The present commercial method for manufacturing organohalosilanes is well known and is described in U.S. Pat. No. 2,380,995—Rochow. Rochow discloses the direct reaction of an organo-halide such as methylchloride with silicon particles in order to produce organochlorosilane. Intermixed with such particles of silicon are particles of copper, thereby forming a reactive mass. In commercial practice this reaction is generally carried out in one of three types of equipment: the stirred bed type of reactor as described in Sellers U.S. Pat. No.2,449,821, the fluidized bed reactor described in Reed, et al U.S. Pat. No. 2,389,931, or the rotary kiln.

Organotrichlorosilanes and diorganodichlorosilanes are the two basic products of the above described direct process reaction. Such compounds are utilized in the production of organopolysiloxane resins as described in U.S. Pat. Nos. 2,258,218 thru 2,258,222. Other products include organopolysiloxane fluids as described in U.S. Pat. No. 2,469,888 and U.S. Pat. No. 2,469,890 as well as the organopolysiloxane elastomers described in U.S. Pat. No. 2,448,756. These patents are generally considered to be the pioneers in the polysiloxane area. Since that time the silicone industry has experienced substantial innovation in this field and a substantial patent literature has evolved relating to the different types of compositions that can be produced from basic organochlorosilanes. It is preferable to produce the diorganodichlorosilanes in a high production manner since they can be utilized most widely, particularly in producing the linear polysiloxane fluids and polymers used in the production of heat cured rubber elastomers and room temperature vulcanizable silicone rubber compositions of various types. Along with these organochlorosilanes there are produced minor amounts of other organochlorosilanes, however, these are not as important as the diorganodichlorosilanes. It is preferable to keep the production of organotrichlorosilanes to a minimum in this process. Since organotrichlorosilanes only produce branch-chained fluids and certain resins, they are fundamentally less useful than the diorganodichlorosilanes discussed above. It is ordinarily necessary that such organotrichlorosilanes be converted to other types of organochlorosilanes before utilizaton in silicone production. Accordingly, it is preferred that in the production of organochlorosilanes by the direct process of Rochow that the weight ratio of triorganochlorosilane to diorganochlorosilane (T/D) be about 0.1 during the production of chlorosilanes by the Rochow process and preferably not exceeding approximately 0.35. However, it has been found that in most commercial manufacturing operations the ratio will be at about the 0.15 level when the reactor is started up with new material but after a period it will rise to an excess of the 0.2 level.

An early solution to this problem was to remove the old silicon particles and the copper catalyst in the reactor and insert new particles whereupon the reaction could be restarted, however, this was expensive in terms of manufacturing costs.

Much research has been directed to finding a method for more fully utilizing the silicon particles in the reactor such that the weight ratio of the organotrichlorosilanes (known as T) to diorganodichlorosilanes (known as D) could be maintained at a desired level for a longer period of time thereby resulting in the maximum utilization of the silicon particles to produce diorganodichlorosilanes. One of the breakthroughs in this area is U.S. Pat. No. 3,133,109—Dotson which is hereby incorporated by reference. Dotson disclosed that the silicon particles could be more fully utilized and the amount of diorganodichlorosilane could be maximized by passing used particles from a fluid bed reactor through an external fluid energy mill. As an alternative to the external fluid energy mill, Dotson also disclosed the passing of the used silicon particles that were recycled from the reactor through a plurality of sonic jets located at the base of the reactor to create a comminution of the particles or the breaking up of the silicon particles as a result of the particles striking each other or the walls of the reactor.

It was found that by utilizing the Dotson method there could be obtained from the same amount of silicon particles a larger amount of diorganodichlorosilane such that the ratio could be kept near the desired 0.15 level and would remain less than the 0.35 level for a longer period of time. However it has also been found that the Dotson process causes under utilization of approximately 12 to 15 percent of the silicon which was introduced into the reactor and which must be removed as waste silicon from the process. It was generally considered that such silicon was poisoned and therefore no longer capable of being utilized to produce diorganodichlorosilanes.

Accordingly it was highly unexpected that the fine particles located in the fluid bed reactor of Dotson could be treated and reutilized to produce diorganodichlorosilanes such that the ratio of T to D did not exceed 0.35 for a sufficiently long period of time and such that the amounts of silicon metal lost as waste from the overall process would be diminished.

In copending U.S. application Ser. No. 132,718 filed Mar. 24, 1980 by Shade there is disclosed a process for treating silicon particles within such a silicon reactor system and thereby improving the usefulness of the silicon metal particles. This application is hereby incorporated by reference. The Shade process comprises a method of treating silicon particles having generally less than forty microns average diameter size whereupon such particles are abraded to remove the surface coating thereon and whereupon the abraded particles can be returned to the reactor for further utilization.

The present invention provides another process for recovering and recycling silicon fines in an organochlorosilane reactor system and can be considered an alternative to the Shade method or can be used in conjunction with the process described by Shade for additional recycling advantages. The process of the present invention comprises a method for classifying direct process contact mass by particle size whereby the most highly poisoned or impure silicon particles are separated from the relatively unpoisoned silicon particles and only such unpoisoned particles are recycled, thereby improving the usefulness of the silicon. Thus instead of disposing the whole mass of spent silicon fines from the direct process, only a small fraction of the spent silicon fines need be disposed at any given time.

Accordingly it is an object of the present invention to provide a process for removing impurities from residual silicon particles and hence for recycling silicon metal particles more beneficially in an organochlorosilane manufacturing process.

SUMMARY OF THE INVENTION

In a process for recovering silicon metal from an organochlorosilane reactor, fine effluent powder (direct process contact mass) is directed to one or more mechanical cyclones for recovery. This fine effluent powder is generally the spent reaction mass from a reactor which produces trichloro-organosilane and diorgano-dichlorosilane products. Crude T and D products are recovered from the top of the cyclones and these products may contain small amounts of "very fine" entrained particles therein.

The remainder of the reaction mass is treated pneumatically in the mechanical cyclones and is directed to a receiving hopper for alternate disposition. Any number of cyclones may be used however it is preferable that two cyclones be used in a commercial process.

According to the process of the present invention the effluent contact mass powder, which is often referred to as silicon fines, contained in the receiving hopper is then directed to an aerodynamic centrifugal classifier. Such a classifier is an apparatus capable of classifying and segregating the cylclone fines into discrete fractions according to particle size. In the most general case, relatively coarse fines are recycled to the organochlorosilane reactor and the finest fraction is discarded or otherwise disposed. It has been found that this so called finest fraction contains the predominantly highest percentages of non-silicon impurities such as carbon, copper, etc.

A determination must also be made as to which size fraction will be discarded and which will be recycled. This determination is dependent upon two competing considerations. The economics of running a commercially practical facility require that as much of the elementary silicon as possible be saved and recycled. However, the greater the percentage of silicon that is recycled the more impurities that are likewise recycled to the reactor system thus gradually decreasing the efficiency of said reactor. The other competing factor relates to the efficiency of the classification system. In accordance with the process presented hereinbelow it is possible to determine the relative amounts or percentages of impurities found in the various fractions of fines powder which have been classified by size. As state above it is generally true that the finest fractions contain the greatest percent of impurities based upon the total weight of the selected fraction. Therefore, in selecting a suitable cut point for segregating the coarse fraction from the fine fraction, there must first be a determination as to where the efficiency of classification overcomes the economics of silicon recycling. The amount of recycled silicon, therefore, will be wholly dependent upon the selection of a cut point which determines the relative magnitude of the segregated fines particles which will be discarded.

The silicon fines which have been chemically analyzed for various impurities can be further analyzed with a particle size distribution (PSD) analyzer in order to determine the relative weight percent of the total silicon fines which can be found in any selected fraction. If for example a fraction contains only a few percent of the total mass of the material it may be relatively more beneficial to discard this fraction rather than recycling it if it also contains a relatively high concentration of impurities.

For example, in a typical process, particle size distribution analysis might indicate that approximately 80% of the particles in the effluent contact mass have a diameter greater than about 5 microns. Therefore if 5 microns were selected as a cut point, approximately 20% of the contact mass would be segregated into the fine fraction. Elemental chemical analyses might further indicate, for example, that this finest fraction also contains, approximately 70% of the total non-silicon impurities to be found in the direct process contact mass. Thus a 5 micron cut point would achieve the recycling of 80% of the contact mass and disposal of the relatively impure 20% fraction.

This so called cut point is achieved by adjusting the various process parameters utilized with such particle classifiers. For example, for cetrifugal classifiers the speed of the classifier can be adjusted so as to determine which fractions of material are segregated. Additionally, the flow of classifier medium such as air, nitrogen or any inert gas can be adjusted so as to carry off the selected segregated fractions.

Thereafter, the relatively coarse fines (i.e. those containing the least amount of non-silicon impurities) are recycled to a feed hopper for reuse in the same or different organohalosilane reactor as well as other uses such as the production of trichlorosilane. On the other hand the finest fraction which has been segregated can be discarded or environmentally disposed or may also be used for such processes as trichlorosilane production as well as copper recovery processes.

DESCRIPTION OF THE PREFERRED EMBODIMENTS

The organic halides which react with silicon in the process of the present invention have the formula:

$$RCl \qquad (1)$$

where R is a monovalent organic radical, such as a hydrocarbon radical selected from the class consisting of alkyl radicals, e.g., methyl, ethyl, propyl, butyl, octyl, etc. radicals; aryl radicals, e.g., phenyl, naphthyl, tolyl, xylyl, etc. radicals; aralkyl radicals, e.g., phenylethyl, benzyl, etc. radicals; alkenyl radicals, e.g., vinyl, allyl, etc. radicals; alkynyl radicals, e.g., ethynyl, propynyl, etc. radicals; cycloalkyl radicals, e.g., cyclohexyl, cycloheptyl, etc. radicals; and cycloalkenyl radicals, e.g., cycloheptenyl, cyclohexenyl radicals, etc. The preferred organic chlorides within the scope of Formula 1 are chlorobenzene, methyl chloride and ethyl chloride, with the preferred specific organic chloride being methyl chloride.

When the organic chloride of Formula 1 reacts with elemental silicon, the products formed consist primarily of organochlorosilanes having the formula:

$$R_nSiCl_{4-n} \quad (2)$$

where R is as previously defined and n is an integer equal to from 1 to 3. Specific examples of organochlorosilanes include methyltrichlorosilane, dimethyldichlorosilane and trimethylchlorosilane which are formed from methyl chloride; phenyltrichlorosilane, diphenyldichlorosilane and triphenylchlorosilane which are formed from chlorobenzene; and various other organochlorosilanes such as diethyldichlorosilane, dibenzyldichlorosilane, vinyltrichlorosilane, etc. which are formed from the appropriate organic chloride.

The elemental silicon with which the organic chloride reacts is in finely divided form and for optimum results, the silicon in the reactor has an average particle diameter in the range of from about 20 to 200 microns. Preferably at least 25 percent by weight of the silicon particles have actual diameters in the range of from 20 to 200 microns. While the reaction will proceed in the absence of a catalyst, it is preferred that the powdered silicon be mixed with powdered copper as taught in the aforementioned U.S. Pat. No. 2,380,995—Rochow. The powdered copper acts as a catalyst for increasing the rate of reaction between the organic chloride and the silicon. When copper powder is employed, the copper is present in the range of from about 0.5 to 20 percent, and preferably from about 2 to 10 percent, by weight, based on the weight of the finely divided silicon. One form of copper powder catalyst useful in the practice of the present invention is the powdered copper partially coated with copper oxide which is described in U.S. Pat. No.2,443,902—Ferguson et al. and which has an average particle size in the range of about 1 to 20, and preferably 1 to 10, microns. In addition to the use of a catalyst such as copper, a promoter such as zinc metal, as taught in U.S. Pat. No. 2,464,033—Gilliam, can also be employed with the silicon and copper. Where such a promoter is employed, it is used preferably in amounts equal to from about 0.05 to 0.5 percent based on the weight of silicon.

As pointed out previously, it is important to maintain the ratio of the product of the organotrichlorosilane to diorganichlorosilanes (T/D) in the product stream coming from the reactor at as low a value as possible. Usually as the reaction proceeds with fresh silicon and fresh copper particles, the T/D ratio drops to 0.1 to 0.2 where it stays for a long period of time and then slowly increases to above 0.2 and the higher values unless it is retarded. Usually the method of retarding the increase of the T/D ratio is to insert or replace the spent or used silicon particles and silicon-copper particles in the reactor bed with new silicon particles and new silicon-copper particles.

Dotson found, for instance in the patent mentioned previously, that the T/D ratio could be maintained for a longer period of time at the level of below 0.35 by comminuting the particles of silicon in the reactor to smaller particles utilizing a fluid energy mill external to the reactor and then passing them back to the reactor after they have been comminuted. Another method was by the utilization of sonic jets in the reactor to comminute the particles in situ as pointed out in the patent.

By comminuting, Dotson refers to such terms as crushing, pulverizing, disintegration and will include breakage of individual particles of the silicon-copper mixture from compression, impact, grinding, or attrition. However, it was found with the use of the fluid energy mill or the jet mill internal to the reactor, even though the T/D ratio would be maintained below 0.35 for a longer period of time, nevertheless, after a time the ratio would increase above that level. It was commonly thought that the silicon particles of size less than about 40 microns average diameter were poisoned and were to be dumped or disposed and fresh silicon and copper particles were inserted into the reactor to take the place of such silicon fines. It should be noted that such silicon-copper fines were not comminuted by the jet mill of the Dotson patent. The reason for this was two-fold. Dotson disclosed that silicon particles could be comminuted by being passed through a jet mill or a fluid energy mill and more preferably through a jet mill at the bottom of the reactor, such that the T/D ratio could be maintained at a low level for a longer period of time and wherein the silicon particles could be useable for the production of diorganodichlorosilane for a longer period of time. However, Dotson failed to appreciate that particles of 40 microns or less in average diameter would not be comminuted or subjected to the communition process of his patent. It is speculated that even with the jets at the bottom of the reactor facing each other, particles of 40 microns or less average diameter would not have enough momentum such that when they collided with each other or with the side of the reactor they would be comminuted. Further it was found that particles of 40 microns or less could generally follow the stream path of the gases passing through the jet mill and flow upwards along the path of the gas up through the reactor without striking each other with very much force. It was only the coarser particles that had the momentum to break the path of the upward flow of the gases and fly at each other so as to be comminuted.

Accordingly, when the silicon-copper particle mixture in the reactor has been used for some time and the T/D ratio has gone beyond permissible levels, the silicon-copper particles in the reactor were considered poisoned and were dumped. New virgin silicon particles were then inserted into the reactor. Dotson did not recognize the reason why the silicon particles needed to be comminuted after they had been used in the process for some time and why the comminution maintained or dropped the T/D ratio to a low level for a longer period of time. Other workers skilled in the art also did not know why the silicon-copper mixture became poisoned even after it had been used for a period of time and there was much speculation and work in the field.

The present invention recognizes that it is possible to recover and recycle silicon from spent silicon fines contact mass or from the reactor bed of a direct process organohalosilane reactor, while at the same time keeping the T/D ratio at an acceptable level. This is possible only by selectively segregating and recycling only the relatively purest, coarse fraction of silicon fines.

Figure 1:
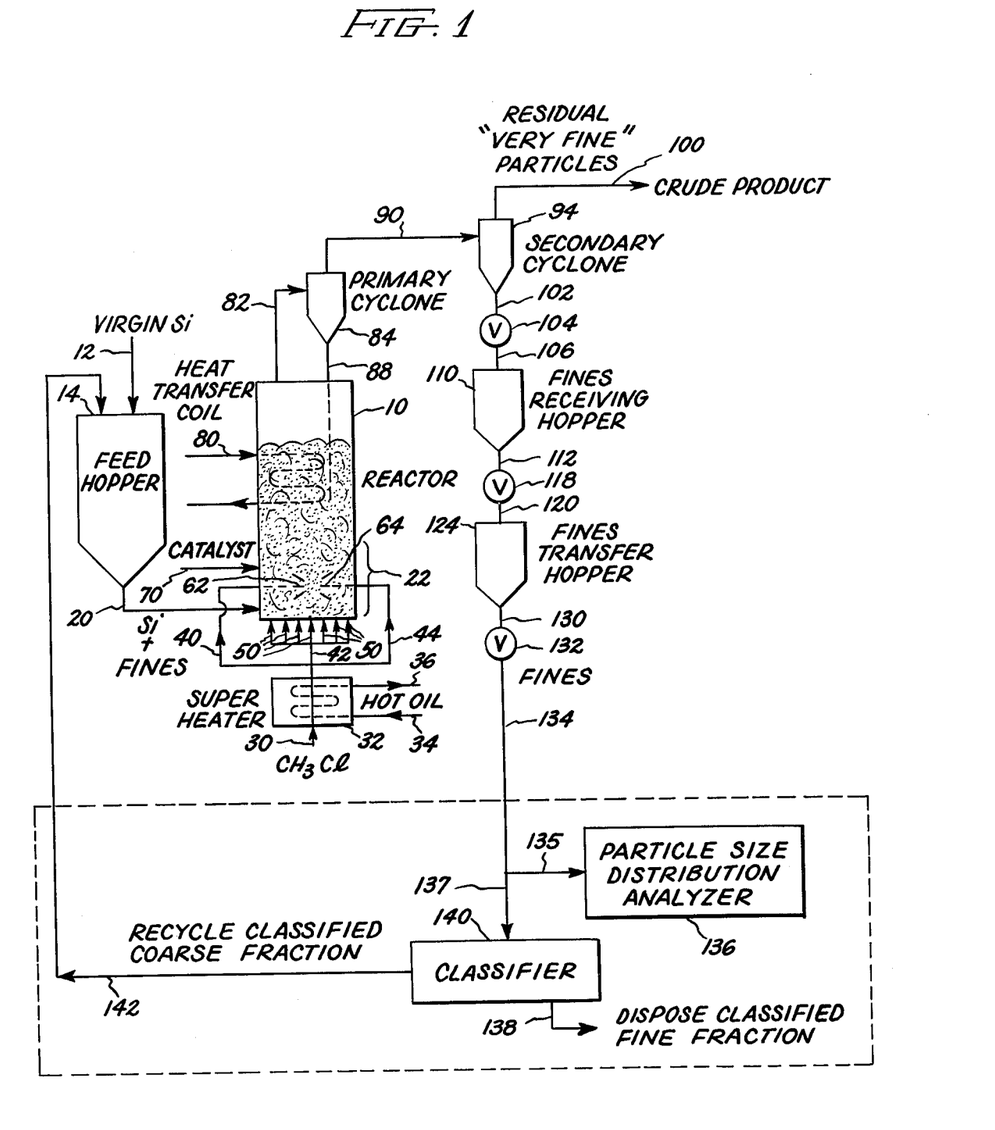
FIG. 1 is a schematic diagram of the process of the present invention as applied to one organohalosilane reactor.

PROCEEDING TO FIG. 1

FIG. 1 is a preferred process of the instant case as applied to a single reactor. FIG. 1 contains silicon reactor 10. Virgin silicon material is fed through line 12 into feed hopper 14. Such virgin silicon material is in the form of silicon particles of an average particle diameter of anywhere from less than 20 to greater than 300 microns in average diameter. The mean particle size is 100 to 150 microns in diameter. The silicon particles pass from feed hopper 14 to line 20 to the bottom portion 22 of reactor 10. Methyl chloride is passed from a supply tank to line 30 into super heater 32 which is heated by hot oil passing through lines 34 and 36. The methyl chloride or any organo-halide used in the reactor is preferably heated to temperature of approximately 250° to 300° C. Organic-halide then passes out of heater 32 into three lines 40, 42, 44. Then the methyl chloride in line 42 passes through jets in combination 50 at the bottom of the reactor. The methyl chloride in lines 40 and 44 passes into jets 62 and 64 and in combination with jet 50 to cause the coarser silicon particles as mentioned previously in accordance with Dotson to be comminuted against each other. It should be noted that the reactor area is filled with copper particles through line 70. The transfer coil 80 removes heat from the reactor so as to keep the temperature of the reactor within the range of 250° to 350° C. In accordance with the instant invention, silicon fines and product are removed from the reactor through line 82 and passed into cyclone 84 wherein the coarser particles are returned through line 88. Silicon particles of less than 50 microns in average diameter as well as chlorosilane product is taken out through line 90 and passed to a second cyclone 94. From second cyclone 94 there is taken through line 100 an organosilane product and some particles of silicone and copper (silicon particles predominately 2 or 3 microns or less in diameter size) and unreacted organic chloride. The silicon fines and silicon copper fines as disclosed previously are separated in second cyclone 94 and passed through the line 102, valve 104, and through line 106 into receiving hopper 110 and are taken through line 112, valve 118, and line 120 into transfer hopper 124. From transfer hopper 124 they are passed from line 130, valve 132 to line 134.

In accordance with the disclosure of the present invention, a portion of the silicon fines in line 134 will pass through line 135 to a Particle Size Distribution Analyzer 136 as will hereinafter be described. This PSD analyzer will indicate the relative amount of silicon fines contact mass to be found in various selected fractions.

The remaining and major portion of silicon fines from line 134 will pass through line 137 to classifier 140. Classifier 140 is apparatus effective for segregating a fine fraction of the silicon fines contact mass from a coarse fraction of the same material at a selected cut point. In commercial methylchlorosilane reactor systems such a cut point will ordinarily be, approximately, 3 to 20 microns. Classifier 140 will preferably be an aerodynamic or centrifugal classifier, examples of which will be described below. However it is to be understood that any classifier apparatus effective for segregating the fine and coarse fractions at the desired cut point will be suitable.

Line 138 indicates the path of travel for the relatively impure finest fraction which is released from the system and disposed or reused for other purposes. The relatively purer coarse fraction leaves classifier 140 through line 142 for recycling to the same or different reactor system. On the average one could expect approximately 50 to 95% of the fines material to be recycled to the reactor system. Of this material, approximately 80 to 98 percent by weight would be the desirable elementary silicon.

Figure 2:
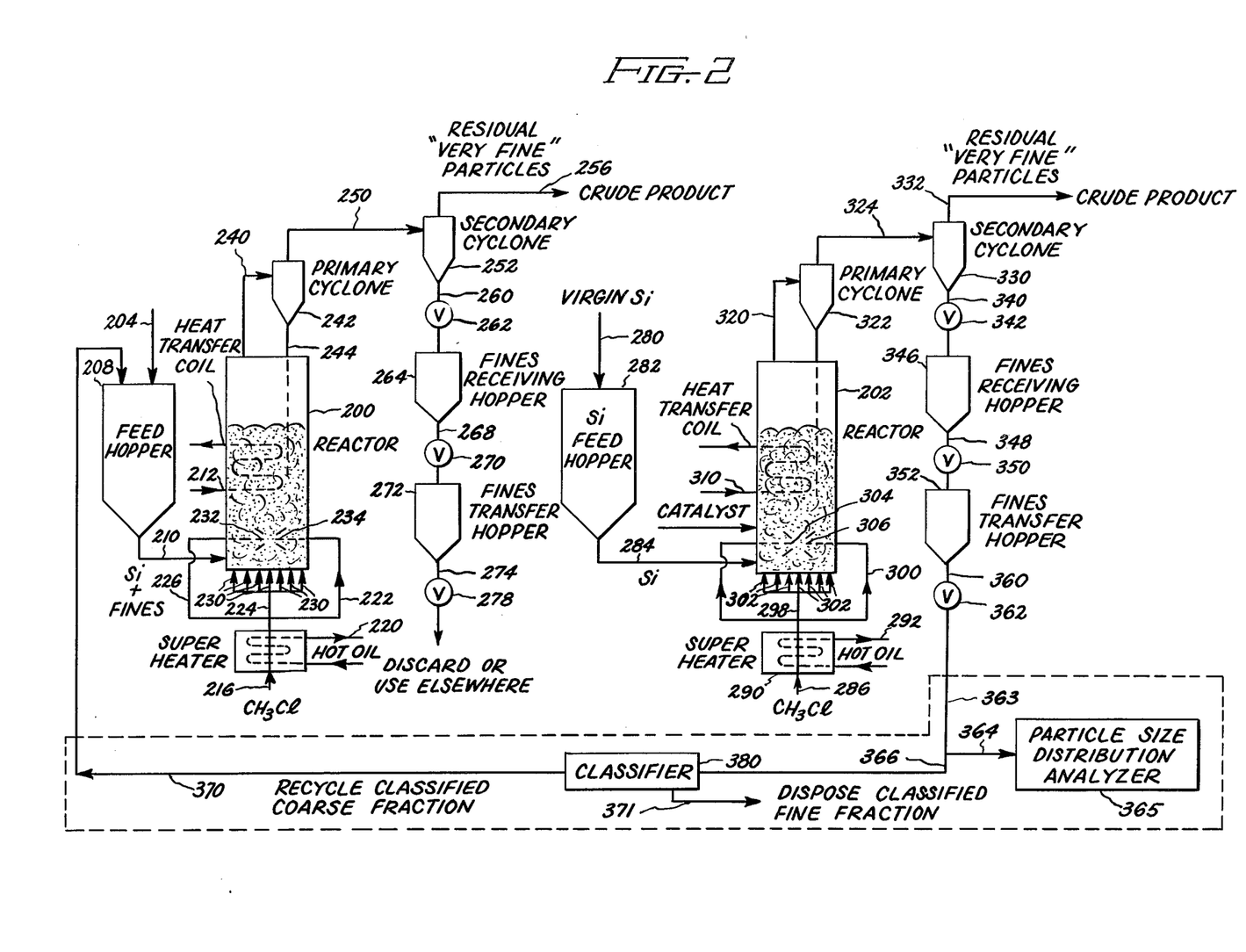
FIG. 2 is a schematic diagram of the process of the present invention as applied to two reactors.

A preferred application of the process of the instant invention is disclosed in FIG. 2, where two reactors 200 and 202 are utilized. Two reactors are preferred in silicone plants since if one ceases to function for some reason the other can still produce silicone materials to keep most of the process lines in the plant open or working. In FIG. 2, virgin silicon particles are fed through line 204 into feed hopper 208 and then line 210 into reactor 200. Reactor 200 has heat transfer coil 212 to remove heat from the reactor so as to maintain the temperature in the reactor from 250° to 350° C. As disclosed with FIG. 1, methyl chloride or another organo-halide is fed into line 216 through superheater 218 which is heated by hot oil passing through line 220; the organo-halide or methyl chloride passes through line 216 to lines 222, 224, 226 through jets 230, 232 and 234 so as to comminute the coarser particles introduced through line 210, in accordance with the disclosure of Dotson. Organochlorosilane products along with silicon particles and organic chloride are removed through line 240 into primary cyclone 242 wherein the coarser particles are returned to the reactor through line 244 and wherein the organochlorosilane products along with the silicon fines are passed on through line 250 into second cylcone 252. Organochlorosilane product along with some very fine particles predominately less than 2 or 3 microns in size as well as organic chloride is removed through line 256. The silicon fines are collected in secondary cyclone 252 and then passed through line 260 and valve 262 to receiving hopper 264. After a sufficient amount has accumulated in the receiving hopper 264, the fines are passed through lines 268 and valve 270 into fines transfer hopper 272. They are then passed from transfer hopper 272 through line 274 and valve 278 to a dumping place where they are discarded.

The second reactor 202 operates similarly: virgin silicon material particles pass through line 280 into feed hopper 282. From feed hopper 282 the silicon passes through line 284 to the bottom of reactor 202. At the bottom of reactor 202 organic-halide or methyl chloride passes through line 286 after being superheated in superheater 290 which is heated by hot oil coil 292 into lines 296, 298, and 300. The methyl chloride from lines 296, 298 and 300 passes into jets 302, 304, and 306. The near sonic velocity of the methyl chloride passing through these jets 304 and 306 causes comminution of the silicon particles entering the reactor through line 284.

As was the case with the reactor in FIG. 1 any coarse silicon particle that happens to find its way from the top part of the reactor to the lower part of the reactor is comminuted. The heat transfer coil 310 takes out heat from the reactor. The reactor is usually maintained at a temperature of 250° to 350°. Organochlorosilane products along with organic-halide and silicon particles are removed through line 320 into primary cyclone 322. The coarse particles are returned to reactor 202 from primary cyclone 322. The organochlorosilane product, organic chloride, and silicon fines from primary cyclone 322 pass through line 324 into secondary cyclone 330. From secondary cyclone 330 there passes through line 332 organochlorosilane product, and some very fine particles (2 or 3 microns or less in size) and organic chloride. The silicon fines are collected in secondary cyclone 330 and then are passed through line 340 and valve 342 into receiving hopper 346. From receiving hopper 346 after sufficient silicon fines of the instant case are collected they are passed through line 348 and valve 350 into transfer hopper 352 and from transfer hopper 352, after a sufficient amount has been collected, the silicon fines are then passed through line 360 and valve 362 to line 363, from which a portion of the silicon fines can be diverted through line 364 to Particle Size Distribution Analyzer 365. The remaining and major portion of silicon fines from line 363 will then pass through line 366 to mechanical classifier 380 which preferably will be an aerodymic or centrifugal classifier as described above. The relatively impure finest fraction of silicon contact mass material which has been segregated by classifier 380 will be disposed through line 371. The relatively coarse fraction can then be recycled through line 370 to first reactor 200.

Figure 3:
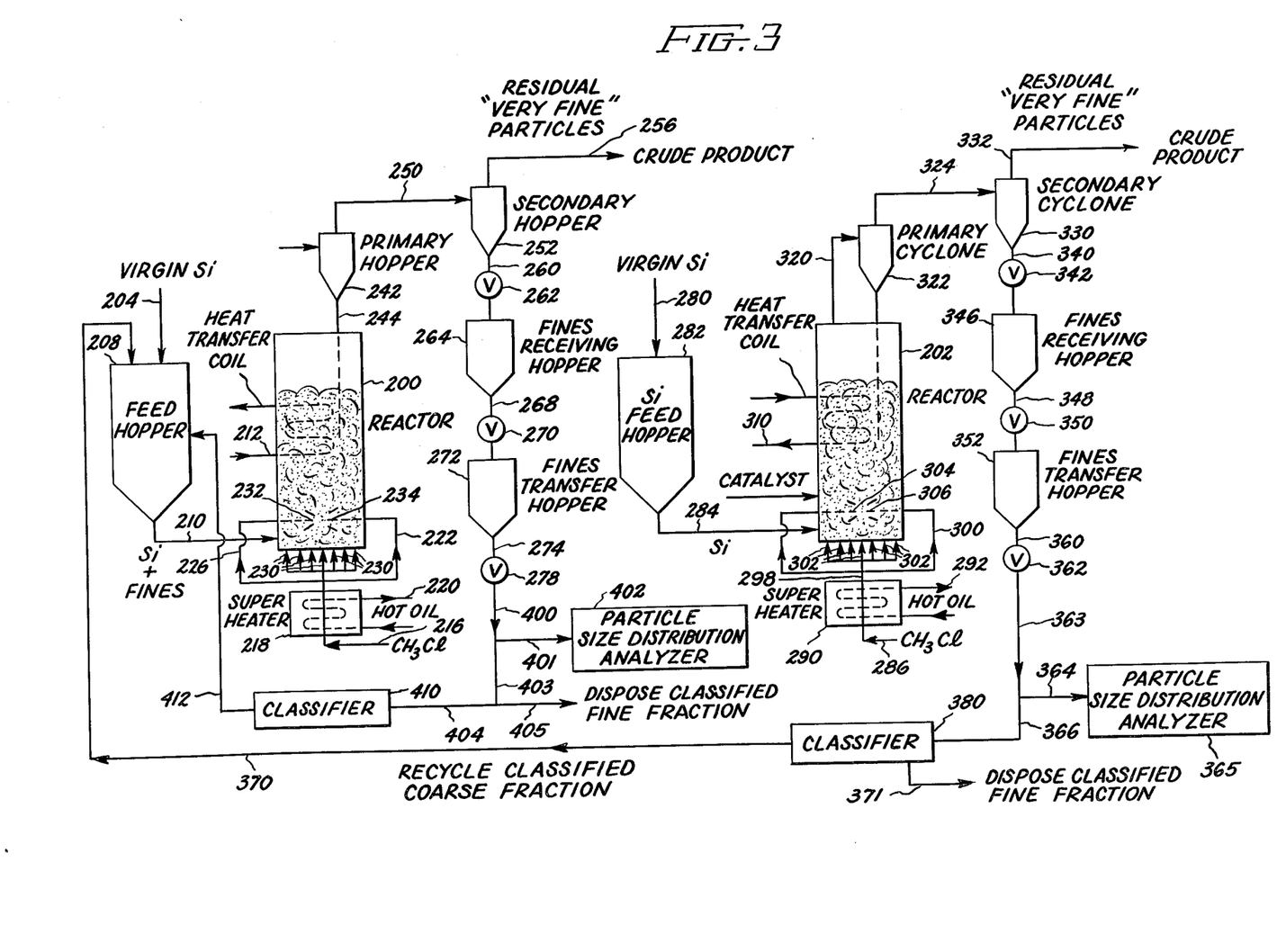
FIG. 3 is a schematic diagram of an alternate and preferred embodiment of the process of FIG. 2.

FIG. 3 is a modification of the process of FIG. 2 and is the most preferred embodiment. FIG. 3 represents an embodiment of the present invention for a two reactor system wherein the fines classification process is carried out for each reactor. PSD Analyzer 365 in combination with Classifier 380 are effective for recovering useful silicon from the contact mass produced from reactor 202. This material can be recycled to feed hopper 208 as well as feed hopper 282. Similarly, silicon fines from reactor 200 can be treated with PSD 402 in combination with classifier 410 wherein the coarse fraction can be directed through line 412 back to feed hopper 208.

It should also be noted that the above process for treating the silicon fines has been shown as a continuous process in FIGS. 1, 2, 3. It is, of course, obvious that in a semi-batch process the same principles would apply and the process of FIGS. 1, 2, or 3, would be simple to implement. A batch process would be still easier to implement in accordance with the instant disclosure but it would be less economical than the semi-continuous process. Such batch processing would be particularly useful when the process of the present invention is utilized to recover silicon from the contact mass material found in the direct process reactor bed. Accordingly, it is preferred to run the production of organochlorosilane in a continuous manner in the process of FIGS. 1, 2, or 3 and there may be utilized two reactors to carry out the process whereby the recycled fines are reutilized in either reactor as the case may be and dependent upon which reactor produces the most fines.

It should also be appreciated that the present process can be implemented with more than two reactors in line and as many as necessary to run a particular silicone plant. It should be appreciated that by utilizing the process of the instant case it is possible to recycle a significant amount of silicon that is submitted to the reactor such that only about 0.5 to 10 percent of fresh virgin silicon that is introduced to the reactor system is lost as waste from the reactor.

Particle Size Distribution Analysis (PSD Analysis) described above can be accomplished by any of several methods. Coulter Electronics, Inc. provides a Coulter Counter Model TA II which is suitable for such analysis. The Coulter Counter suspends the fines particles in a clean electrolyte, e.g. 2% NaCl in water and then electronically determines the particle size distribution.

Another example is the Leeds and Northrup Microtrac PSD Analyzer, Model 7991, wherein the sample powder is transported across a continuous laser beam and the analysis is accomplished by measuring the degree of scattering of the beam by the particles.

The mechanical classifiers are those devices capable of segregating the contact mass into a fine and coarse fraction at the desired cut point. For particles having a diameter greater than about 100 microns, sieve screens could be used. However, in the present invention, the cut point is generally much smaller than this, therefore centrifugal or aerodynamic classifiers are the preferred devices.

The Alpine Multiplex 100 MZR (lab model) is an aerodynamic and centrifugal classifier which segregates the fine and coarse fractions by varying the carrier gas flow rate and the rotor speed. The centrifugal force generated by the rotor draws the large (heavy) particles to the periphery while the drag force due to the carrier gas draws the particles toward the center where they may exit the classifier with the carrier gas. In a commercial scale model (Model 400 MPS) the classifier speed is fixed but the cut point can be changed by adjusting the position of the guide vanes.

Another classifier is the Majac Lab Model A-12 which also fractionates the materials at the desired cut point by varying the carrier gas flow rate and the rotor speed. Majac also manufactures a commercial scale classifier designated Model C-24.

The following examples are illustrative of several aspects of the present invention and are not in any way intended to limit the scope of the invention.

EXAMPLE 1

Approximately 10 pounds of commercial secondary cyclone fines from a direct process methylchlorosilane reactor were obtained and subjected to elemental analysis by atomic absorption (AA) and alkaline fusion (gravimetric). The analysis revealed the following approximate composition of the fines mass, by weight:

| Component | Weight % |
|---|---|
| Si | 78.6 |
| Cu | 3.6 |
| C | 1.05 |
| Fe | 2.8 |
| Al | 1.2 |
| Zn | 0.4 |
| Ca | 0.5 |
| Sn | 0.4 |
| Pb | 0.1 |
| P | approx. 0.1 |
| Other* | approx. 11.25 |

*The other components were predominately Cl, H, and O but there are present other trace metallic impurities such as Ti, Mn, V, Zr, Ni, Mg, Cr, B, Mo and others. Total organic and inorganic carbon content was determined by pyrolysis.

The aerodynamic fractionation (classification by particle size) of 10 lbs. of fines was carried out at Majac Division, Donaldson, Inc., St., Paul, MN by using a laboratory Model A-12 Acucut Classifier with argon as carrier gas. Argon was substituted for conventionally employed air to minimize the fire and explosion hazard associated with finely divided contact mass material. To minimize carrier gas consumption, a polyethylene tent was erected to completely enclose the apparatus, thus providing recycle capability for the argon gas.

Next, the material was classified by the centrifugal classifier into discrete fractions according to particle size as given below. Each designated fraction contains essentially only those particles having a diameter less than the desired particle diameter. Thus for example, 95% of Sample C contains particles ranging in size from, approximately, 10 to 15 microns diameter, and Sample C comprises approximately 15.1% of the total feed amount, by weight.

| Fraction Designation | Nominal Desired Fraction Size in Microns | Particle Size Analysis of Fraction | Weight of Feed Fines |
|---|---|---|---|
| A | <5 | 94% < 5 microns | 12.1 |
| B | 5–10 | 95% <10 microns | 16.9 |
| C | 10–15 | 95% <15 microns | 15.1 |
| D | 15–20 | 96% <20 microns | 40.6 |
| E | >20 | 97% >20 microns | 13.2 |

It can be seen that 97.9% of the feed material was recovered in this classification example. The unaccounted material (approximately 2.1% of original feed) was believed to be partly in the final filter and partly in the classifier chamber. Subsequent elemental analysis of each fraction gave the following results:

| Fraction Designation | Nominal Particle Size | Weight % | | | | | | |
|---|---|---|---|---|---|---|---|---|
| | | Si | C | Cu | Fe | Zn | Al | Ca |
| A | < 5 microns | 62.7 | 2.04 | 9.1 | 4.1 | 1.0 | 2.1 | 0.7 |
| B | 5–10 microns | 76.6 | .993 | 6.2 | 2.4 | 0.5 | 1.2 | 0.5 |
| C | 10–15 microns | 82.5 | .698 | 3.9 | 2.7 | 0.3 | 1.5 | 0.6 |
| D | 15–20 microns | 85.6 | .601 | 4.2 | 2.2 | 0.3 | 1.1 | 0.5 |
| E | >20 microns | 87.3 | .638 | 5.7 | 2.5 | 0.2 | 1.2 | 0.6 |

Thus it can be generally seen that the finest fractions (e.g. A and B) contain the highest levels of impurities and the least amount of silicon. Methylchlorosilane direct process reaction effectiveness was then determined in a laboratory one-inch stirred bed reaction system for both classified and unclassified secondary cyclone fines in order to determine the efficacy of the process of the present invention. The reaction zone temperature was approximately 300° C. to which was charged 50 grams of fines. Additionally, the CH$_3$Cl feed rate was maintained at 12.5 grams per hour.

Crude methylchlorosilane product effluent was analyzed hourly by gas chromatography to determine product distribution and T/D ratio (wgt. % ratio of CH$_3$SiCl$_3$/(CH$_3$)$_2$SiCl$_2$). The starting fine material as well as classified fractions were all reacted in both stirred (helical agitator rotating at 60 RPM) and static (fixed bed) modes. Rate was determined by weight of crude product recovered per unit time. Percent Si utilization was monitored by subtracting out Si consumed via reaction to form methylchlorosilanes from initial Si level (as determined by alkali fusion or AA analysis). The following direct process reaction selectivity data was generated in the unstirred, i.e. static, mode of reaction. For each fraction the table indicates the T/D ratio at any given percent silicon utilization level.

| Fraction (microns) | T/D @ % Si Utilization | | | | | | | |
|---|---|---|---|---|---|---|---|---|
| | 10 | 20 | 30 | 40 | 50 | 60 | 70 | 80 |
| < 5 | .09 | .06 | .13 | .17 | .22 | .48 | 1.7 | 4 |
| 5–10 | .062 | .044 | .044 | .047 | .056 | .070 | .094 | .192 |
| 10–15 | .054 | .045 | .045 | .047 | .051 | .064 | .094 | .128 |
| 15–20 | .052 | .041 | .042 | .046 | .052 | .062 | .090 | .28 |
| >20 | .056 | .049 | .050 | .055 | .064 | .077 | .11 | — |
| unclassified fines | .055 | .051 | .053 | .059 | .078 | — | — | — |

Likewise, stirred mode reactions of starting material and classified fractions gave the following T/D versus percent silicon utilization profile:

| Fraction | T/D @ % Si Utilization | | | | | | | |
|---|---|---|---|---|---|---|---|---|
| | 10 | 20 | 30 | 40 | 50 | 60 | 70 | 80 |
| Unclassified Fines | .053 | .055 | .057 | .062 | .075 | .098 | — | — |
| Classified < 5 microns | .10 | .074 | .094 | .095 | .11 | 1.10 | * | * |
| Classified 5–10 microns | .066 | .048 | .043 | .042 | .043 | .050 | .069 | .12 |
| Classified 10–15 microns | .064 | .045 | .038 | .036 | .043 | .042 | .088 | .13 |
| Classified 15–20 microns | .051 | .042 | .037 | .042 | .042 | .047 | .055 | .124 |
| Classified >20 | .053 | .042 | .041 | .043 | .046 | .050 | .070 | .24 |

*Reaction terminated @ 67% Si Utilization since the T/D ratio reached 4.0.

Presenting lab selectivity data (T/D vs. reaction time) showed the following in a stirred mode of operation:

| Sample | T/D @ Reaction Time (Hrs.) | | | | | |
|---|---|---|---|---|---|---|
| | 5 | 7 | 10 | 12 | 15 | 20 |
| Unclassified Fines | .041 | .038 | .042 | .046 | .45 | .5 |
| Classified <5 microns | .10 | .27 | 1.59 | 2.43 | 3.78 | 3.8 |
| Classified 5–10 microns | .044 | .042 | .054 | .094 | .3 | 1.1 |
| Classified 10–15 microns | .047 | .038 | .040 | .042 | .047 | .123 |
| Classified 15–20 microns | .042 | .038 | .037 | .037 | .040 | .046 |
| Classified >20 microns | .047 | .041 | .040 | .041 | .043 | .048 |

Thus it is clear upon an examination of the above data that the finest fraction (nominally less than 5 microns in particle diameter) which comprises approximately 12 weight percent of the secondary cyclone fines, also contains the highest percent of non-silicon impurities and demonstrated the poorest reaction selectivity (T/D) under laboratory direct process reaction conditions. On the other hand, the remaining fractions constituting approximately 88 weight percent of the fines (fractions nominally greater than 5 microns particle diameter) exhibited surprisingly low T/D ratios, for longer periods of time.

Selecting T/D of 0.1 as an arbitrary acceptable selectivity indicator, the above may be summarized as follows:

| Fraction | Time @ T/D <0.1 (Hrs.) |
|---|---|
| Unclassified Fines | 12.5 |
| Classified Fines | |
| < 5 microns | .2.5 |
| 5–10 microns | 12 |
| 10–15 microns | 19 |
| 15–20 microns | 28 |
| >20 microns | 33 |

Thus it can also be seen that the coarser fractions (greater than 5 microns particle size) maintained improved reaction selectivity (low T/D) for substantially longer periods both in terms of available silicon as well as total reaction time. The T/D selectivity of unclassified fines is better (i.e. lower) than that of the finest fraction alone but is poorer than that of classified coarser fraction. It is therefore clear that the silicon fines classification process of the present invention is a useful improvement in the art and provides surprisingly beneficial results.

EXAMPLE 2

Another batch of secondary cyclone fines was classified by using Majac Acucut laboratory classifier model A-12 with nitrogen gas instead of air as classifying medium. A polyethylene chamber enclosed the classifier for continuous recycling of the nitrogen gas. The pressure in the chamber was maintained at a level slightly above ambient to minimize leakage of oxygen into the classifier. Dry nitrogen from cylinders was continuously fed into the chamber. A finned heat exchanger was used to increase the temperature of nitrogen to near ambient and thus compensate for Joule-Thompson cooling of the gas. During classification, the temperature of the recycling gas increased to 110°–115° F. and hence, a portion of the gas was continuously exhausted from the chamber which helped to maintain the gas temperature at 100° F. or below. Particle size measurements were made using a Coulter counter, Model TA-II. The secondary cyclone fines were fractionated into fine and coarse fractions at the following cut points.

| Sample | Approximate Cut Point in microns | Fine Fraction Particle size Analysis | Fine Fraction as weight % of Feed Fines | Coarse Fraction Particle size Analysis |
|---|---|---|---|---|
| F & F$^1$ | 5 | 85% <5.5 microns | 37.8 | 85% >5.5 microns |
| G & G$^1$ | 4 | 85% <4 microns | 24.6 | 85% >4.4 microns |
| H & H$^1$ | 2.8 | 85% <2.6 microns | 8.9 | 85% >3.5 microns |

In the case of fine fractions (F,G,H), each fine fraction contains essentially the particles whose size is smaller than the cut size while in the case of corresponding coarse fractions (F$^1$,G$^1$,H$^1$), each coarse fraction essentially contains the particles whose size is greater than the cut size. For example fractions F and F$^1$ resulted from classification of the fines such that F is the fine fraction and F$^1$ is the coarse fraction where in the fine fraction (F) 85% of the particles are smaller than 5.5 microns in size and they comprise 37.8% by weight of the original secondary cyclone fines, and in the coarse fraction (F$^1$) 85% of the particles are greater than 5.5 microns in size and they comprise 62.2% by weight of the original secondary cyclone fines.

Subsequent elemental analysis of each fraction and that of unclassified fines by the previously described techniques gave the following results.

| Fraction Designation | Weight % | | | | | |
|---|---|---|---|---|---|---|
| | Si | C | Cu | Fe | Zn | Al |
| F | 64.9 | 1.65 | 8.1 | 3.8 | 1.1 | 1.7 |
| F$^1$ | 76.4 | .95 | 4.3 | 3.4 | .8 | 1.3 |
| G | 63.1 | 2.02 | 13.2 | 3.6 | .9 | 1.5 |
| G$^1$ | 81.6 | .97 | 3.1 | 3.2 | .8 | 1.5 |
| H | 51.6 | 3.24 | 11.3 | 4.6 | 1.3 | 3.0 |
| H$^1$ | 77.2 | 1.06 | 4.9 | 2.8 | .6 | 1.5 |
| Unclassified | 74.8 | 1.32 | 4.8 | 3.6 | .6 | 1.8 |

The balance in each case is as mentioned previously in the analysis of secondary cyclone fines in Example 1.

It is clear that the fine fractions contain the higher levels of impurities and less silicon than the corresponding coarse fractions.

The above samples were subjected to the direct process reaction with methylchloride in the apparatus and under the conditions described in Example 1 and their reaction selectivities (T/D) were studied. For example, the unclassified fines, fine fraction G and coarse fraction G$^1$ gave the following profiles. Over a period of fifteen hours, the unclassified fines fraction continuously showed an increase in reaction selectivity, i.e. the T/D ratio continuously increased. The classified fine fraction G showed a dramatic increase in its T/D selectivity, such that unacceptable limits were achieved in approximately six hours. On the other hand, reaction selectivity was studied for the classified coarse fraction G$^1$ which did not reach the T/D level of the unclassified fraction, even after eighteen hours.

EXAMPLE 3

Approximately 4 pounds of commercial secondary cyclone fines from another direct process methylchlorosilane reactor were obtained and a portion of it was classified by aerodynamic/centrigal classification using Alpine American Corp., laboratory model 100 MZR Micro-Plex classifier with nitrogen as carrier gas. Nitrogen was used to minimize fire an explosion hazard. To minimize nitrogen consumption, most of the nitrogen was continuously recycled while a small portion was vented to an exhaust to prevent continuous temperature rise of the gas due to recycling. The speed of the classifier (revolutions per minute) and the flow rate of carrier gas were varied to classify the material into fine and coarse fractions at a desired cut point. The material was classifed such that 67% of the feed was fractionated as a coarse fraction and 33% as fine fraction. The particle size analysis of the fine fraction by Coulter Counter Model TA-II indicated that 85% of the particles were less than 7 microns in size.

Chemical analysis of the unclassified fines, the fine fraction, and the coarse fraction by previously described methods indicated the following:

| Material | Weight % | | | | | |
|---|---|---|---|---|---|---|
| | Si | C | Cu | Fe | Zn | Al |
| Unclassified Fines | 59.9 | 2.88 | 5.3 | 5.3 | 0.5 | 2.1 |
| Fine Fraction | 44.5 | 3.54 | 16.3 | 5.4 | 0.9 | 2.7 |
| Coarse Fraction | 69 | 1.66 | 4.8 | 6.8 | 0.6 | 2.1 |

It is clear that the fine fraction contains the highest levels of non-silicon components and the least amount of silicon.

The above samples were subjected to the direct process reaction with methylchloride in laboratory apparatus and under the conditions described previously and their reaction selectivities were examined. It was found once again that the finest fraction exhibited the worst reaction selectivity compared to the unclassified fines while the coarse fraction had the relatively better reaction selectivity (i.e. the lowest T/D ratio).

EXAMPLE 4

Approximately 5 pounds of reactor bed powder from a direct process commercial reactor were obtained and a portion was classified by the method and apparatus described in Example 3. This powder came from within the reactor and not from the secondary cyclone. The reactor bed powder was classified into fine and coarse fractions. The reactor bed powder is much more coarse than the secondary cyclone fines. The secondary cyclone fines normally contain particles whose diameter is usually less than 50 microns. The diameter of reactor bed powder particles can be up to 700 microns.

The powder was fractionated such that 89% weight of the original powder was in the coarse fraction and 11 weight % was in the fine fraction. The particle size analysis of the fine fraction by Coulter Counter indicated that 85% of the powder was less than 14 microns in size. Chemical analysis of the unclassified reactor bed powder, the fine fraction and the coarse fraction indicated the following:

| Material | Weight % | | | | | |
|---|---|---|---|---|---|---|
| | Si | C | Cu | Fe | Zn | Al |
| Unclassified Bed Powder | 83.8 | 0.54 | 1.7 | 2.5 | 0.3 | 1.5 |
| Fine Fraction | 76.3 | 1.14 | 7.3 | 4.9 | 1.5 | 2.3 |
| Coarse Fraction | 89.0 | 0.539 | 1.5 | 1.9 | 0.3 | 1.7 |

It is clear once more that the fine fraction contained the highest levels of non-silicon components and the least amount of silicon.

What we claim as new and desire to have protected by Letters Patent of the United States is:

1. A process for purifying silicon metal contact mass from a direct process organohalosilane reactor system comprising the steps of:
   (a) analyzing a portion of reactor contact mass for particle size distribution;
   (b) classifying said analyzed contact mass into a relatively pure first fraction and a relatively impure second fraction; and
   (c) segregating said first and second fractions.

2. A process as in claim 1, further comprising the step of recycling said relatively pure first fraction to the same or a different organohalosilane reactor.

3. A process as in claims 1 or 2 wherein said organohalosilane reactor system is comprised of one or more methylchlorosilane reactors.

4. A process as in claim 1 wherein said first and second fractions are classified by selecting a fraction cut point such that substantially all silicon particles in said relatively pure first fraction have a diameter size greater than said cut point and substantially all silicon particles in said relatively impure second fraction have a diameter size less than said fraction cut point.

5. A process as in claim 1 further comprising the step of chemically analyzing said portion of reactor contact mass to determine the relative purity of each particle size distributed fraction.

6. A process as in claim 4 wherein said fraction cut point selection is accomplished by preselecting the weight percent of contact mass, based upon the total of said reactor contact mass, which shall reside in said relatively pure first fraction.

7. A process as in claim 1 wherein said segregating step is accomplished by a centrifugal and aerodynamic classifier.

8. A process as in claim 1 wherein said fraction cut is made at, approximately, 3 to 20 microns.

9. A process as in claim 1 wherein said reactor contact mass is secondary cyclone silicon fines.

10. A process as in claim 1 wherein said reactor contact mass is direct process reactor bed powder.

* * * * *